United States Patent [19]
Levine

[11] Patent Number: 5,854,685
[45] Date of Patent: Dec. 29, 1998

[54] HOLOGRAPHIC GAS ANALYZER UTILIZING HOLOGRAPHIC OPTICS

[76] Inventor: Michael S. Levine, 204 N. El Camino Real, E-531, Encinitas, Calif. 92024

[21] Appl. No.: 812,380

[22] Filed: Mar. 5, 1997

Related U.S. Application Data

[60] Provisional application No. 60/012,870 Mar. 5, 1996.

[51] Int. Cl.[6] ............... G01N 21/00; G01J 3/28; G01J 5/02; G02B 5/32
[52] U.S. Cl. ............ 356/440; 356/439; 356/328; 250/339.07; 250/339.12; 359/19
[58] Field of Search ............... 356/436–440, 356/328; 359/15, 19–20; 250/339.12, 339.07

[56] References Cited

U.S. PATENT DOCUMENTS

| | | | |
|---|---|---|---|
| 4,540,282 | 9/1985 | Landa et al. | 356/328 |
| 4,756,622 | 7/1988 | Wong | 356/437 |
| 5,009,493 | 4/1991 | Koch et al. | 356/440 |
| 5,050,992 | 9/1991 | Drummond et al. | 356/328 |
| 5,060,508 | 10/1991 | Wong | 356/437 |
| 5,065,025 | 11/1991 | Doyle | 356/437 |
| 5,068,798 | 11/1991 | Heath et al. | 356/437 |
| 5,153,679 | 10/1992 | Gilby | 356/440 |
| 5,163,332 | 11/1992 | Wong | 356/437 |
| 5,296,911 | 3/1994 | Weyrauch et al. | 356/328 |
| 5,341,214 | 8/1994 | Wong | 356/437 |

*Primary Examiner*—Frank G. Font
*Assistant Examiner*—Jason D. Vierra-Eisenberg
*Attorney, Agent, or Firm*—Lewis Anten, Esq.; Amedeo Ferraro, Esq.

[57] ABSTRACT

The present invention relates to an analyzer for determining the concentration of substances, such as chemicals, present in a fluid medium, such as gas, vapor or liquid, using holographic optics. The analyzer of the present invention is based on the infra red absorbance of the gas, vapor or liquid to be measured, where the optical functions of an infra red absorbance gas analyzer are performed by holographic functional representations of the required optical components.

17 Claims, 6 Drawing Sheets

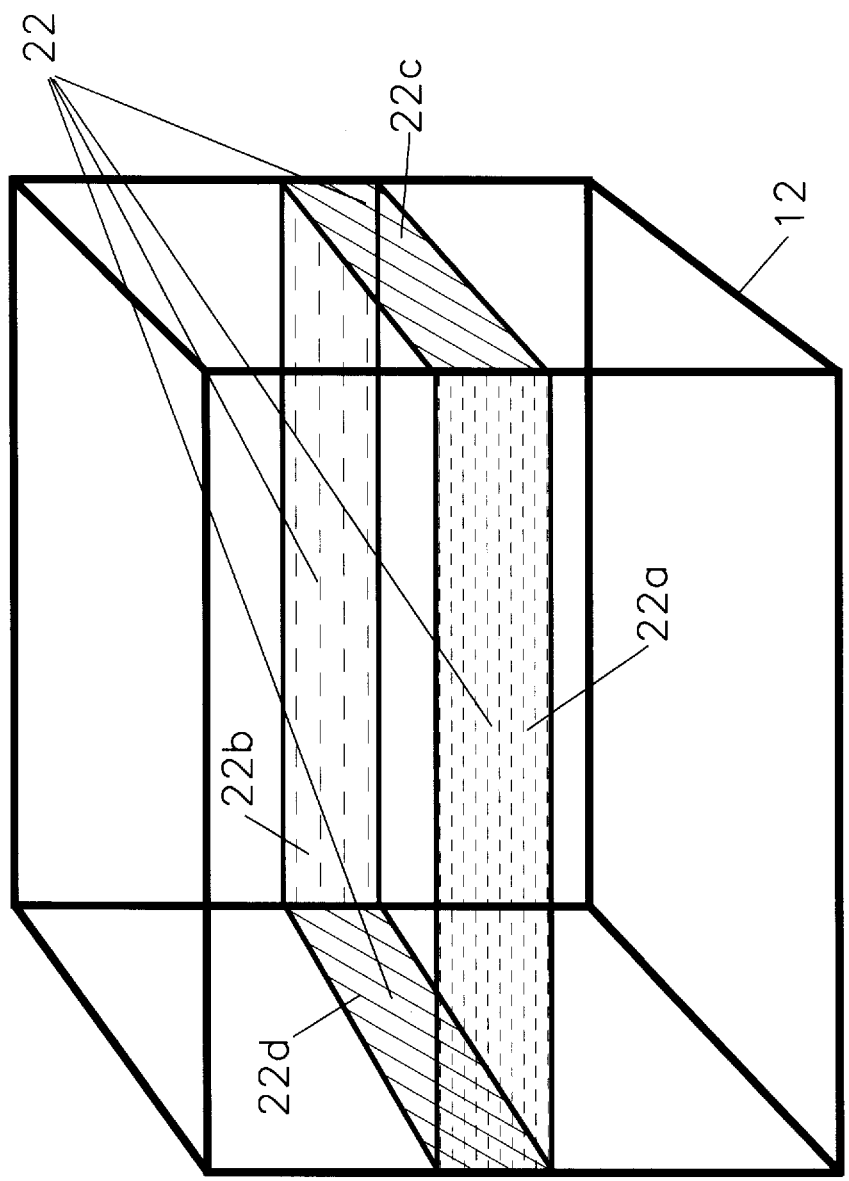

HOLOGRAPHIC GAS ANALYZER UTILIZING HOLOGRAPHIC OPTICS

RELATED APPLICATION

This application claims priority of co-pending United States provisional application Ser. No. 60/012,870 filed on Mar. 5, 1996.

BACKGROUND OF INVENTION

1. Field of the Invention

This invention relates to analyzers for determining the concentration of substances, such as chemicals, present in a gas or vapor, and more particularly to an analyzer utilizing light absorbance of a gas, vapor, or solute in liquid to be measured in association with holographic optics.

2. Description of the Related Art

Chemical compounds absorb light, such as infra red light, with different effectiveness at different wavelengths. Infra red absorbance analyzers use this property to determine the concentration of chemicals in an air and gas or vapor mixture. A beam of infra red light of a discrete wavelength or band known to be absorbed by a chemical is passed through a chamber containing an air and gas or vapor mixture filtered to remove dust. At the end of the infra red light beam path is a photo detector.

When volatile contaminants are introduced into the chamber of a light absorbance gas analyzer, the substances present absorb some of the infra red light, reducing the intensity of the light signal at the photo detector. The amount of attenuation of the light signal is proportional to the concentration of the contaminant and the path length of the beam of light. The light detection circuit is calibrated based on the proportionality between airborne contaminant concentration and the signal absorbance, and outputs a signal or meter value proportional to the contaminant concentration. A reference cell may be used which contains the same optics without the introduction of the gas/vapor (or with a reference gas) to provide a zero reference point.

The prior systems for analyzing a gas or vapor used physical mirrors, reflectors, diffusers, lenses, or light guides, and required either a diffraction grating or a prism to provide monochromatic light. Alternatively, light was limited to a range of wavelengths, or bands by using filters. Narrow slits, focusing and/or directing lenses were used to provide a narrow beam of light. Depending on the inherent absorbance of the compound and the concentration range of interest, a rather long light path length may be required for an adequate minimum detection of the compound. Increasing device sensitivity requires increasing path lengths and therefore a more complex reflective array. In typical instruments, this path length may be on the order of twenty meters. In some specialized devices it is much longer. In order to provide sufficient light path length in a practical sized and often portable device, mirrors and mirror arrays were used to fold the light path within a chamber for the gas or vapor mixture. As instrument response time is a direct function of the volume of the measuring chamber and the rate of air flow through it, reduced chamber size is important to obtain a quick response time.

The characteristics of the optics of the prior art devices such as sensitivity, fragility, and expense, made the prior devices impractical for rugged use and were unworkable in situations where a rapid response was required as the devices could not be made small enough in a practical sufficiently maintainable and affordable manner.

SUMMARY OF THE INVENTION

The present invention relates to analyzers for determining the concentration of light absorbing matter, such as chemicals, present in a gas, vapor or liquid, collectively referred to herein as a "fluid medium." The analyzer of the present invention is based on the absorbance of light, such as infra red light, of the fluid medium to be measured, where the optical functions of the gas analyzer are performed by holographic functional representations of the required optical components. The fluid medium is transparent to the analytical wavelength of light used to quantify light absorbing matter present in the fluid medium.

A basic analyzer in accordance with the present invention comprises a measuring chamber or collecting area for the fluid medium; a monochromatic or polychromatic light source; holographic optics emulating one or more of the following functions: optical slit(s), diffraction grating(s) or equivalent focusing lenses or surfaces, mirror(s); and a light detector/amplifier. In the preferred embodiment of the present invention, holograms are onlaid as single or multiple pads onto the interior surfaces of the measuring chamber. Each holographic pad could have single or multiple functions and may be either a reflective or transmission type as appropriate.

In use of the analyzer of the present invention, a beam of light of a discrete wavelength or band known to be absorbed by a chemical is transmitted through the chamber or area for collecting a fluid medium, such as an air and gas/vapor mixture, to the holographic optics and to the light detector. Any contaminants present in the fluid medium absorb some of the transmitted light, reducing the intensity of the light signal at the light detector. The amount of attenuation of the light signal is proportional to the concentration of contaminants present in the fluid medium and the path length of the beam of light. The path length can be varied by the positioning and number of the holographic optics encountered by the light path. In this manner, the concentration of contaminants present in the fluid medium can be determined.

Some examples of applications of the holographic analyzer of the present invention include chemical process control systems, environmental monitoring systems, automotive emission control systems, indoor air quality monitoring, and industrial hygiene monitoring.

The holographic analyzer of the present invention provides the following advantages over prior systems:

Complex holographic arrays can be easily reproduced, such that functional complexity can be increased without significant increases in costs as the production of reference cells, or multiple wavelength systems would be inexpensive;

High sensitivity in flow through systems can be achieved without sacrificing response time;

A holographic system will not require a larger volume to accommodate more complex light paths;

Holographic optics can be more easily modified for use in harsh environments by application of coatings, or placement of holographic pads behind the surface substrate, such that with proper coatings the present invention could be applied to measurements in static or flowing liquids;

Design flexibility can be further increased using either transmissive or reflective holograms;

Simplicity, and therefore inherent reliability, would be greater than the standard units due to reduced parts count;

A holographic system is simpler, easier to manufacture and therefore would be of lower cost to produce and sell than the devices of the prior art; and The lower cost and reliability of the present invention would facilitate use in applications not currently considered feasible.

These and other advantages of the present invention will become apparent from a review of the accompanying drawings and the detailed description of the drawings.

BRIEF DESCRIPTION OF THE DRAWINGS

FIG. 2a is a schematic representation of another embodiment of a holographic gas analyzer according to the present invention.

FIG. 2b is a top view of FIG. 2a illustrating the configuration of a light path passing through the holographic gas analyzer of FIG. 2a.

DETAILED DESCRIPTION OF THE DRAWINGS

Figure 1:
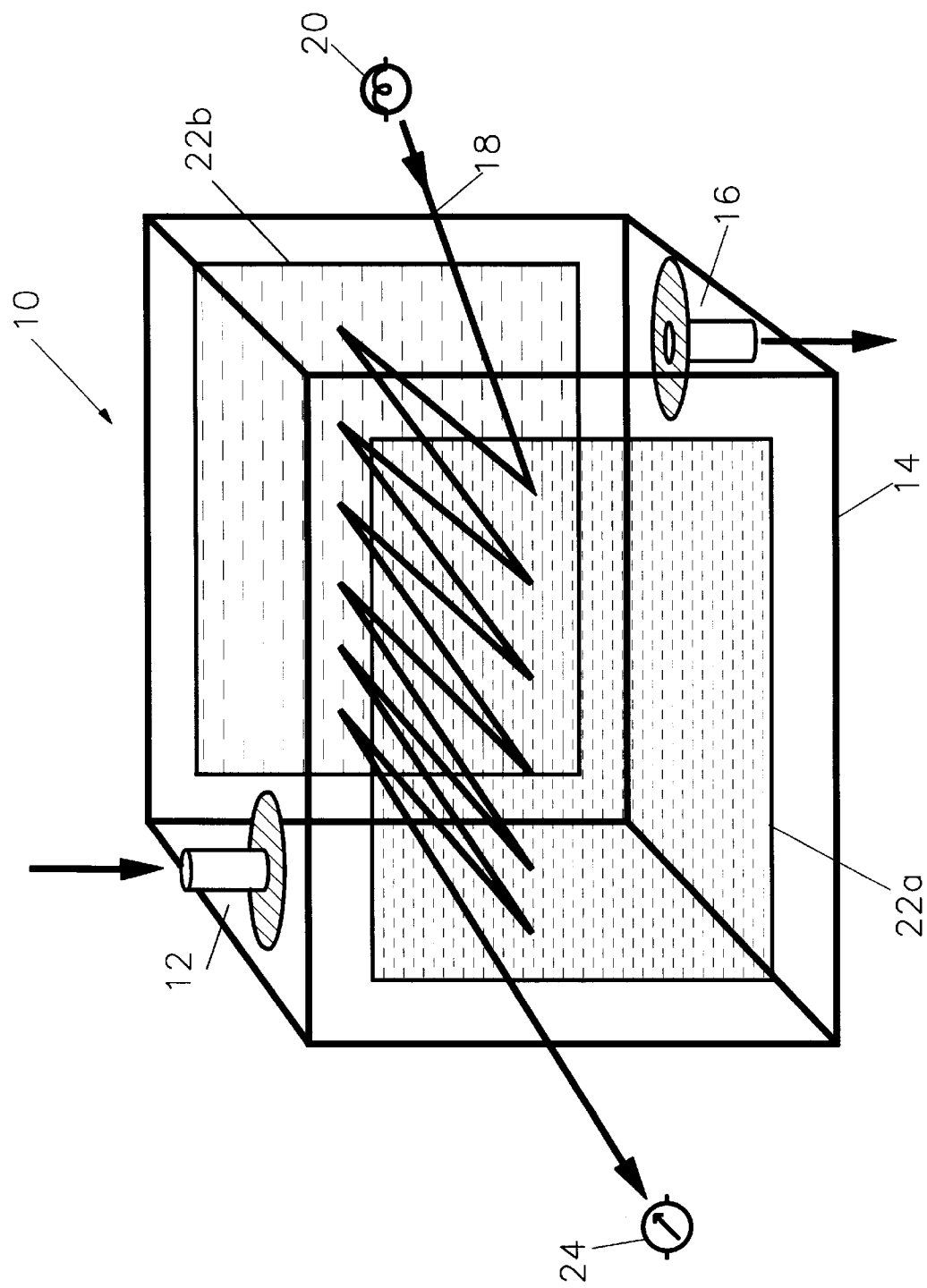
FIG. 1 is a schematic representation of a holographic gas analyzer according to the present invention.

Referring to FIG. 1, a basic embodiment of the holographic gas analyzer system of the present invention is shown and generally referred to by the numeral 10. The holographic gas analyzer 10 comprises a chamber 14, a light source 20, one or more holographic reflective pads 22a and 22b, and a detector 24, such as a photodetector which may include an amplifier. Infra red detectors are well known in the art and detectors appropriate for this application are commercially available by a number of companies including Electo-Optical Systems, Inc. of Phoenixville, Pa.

A fluid medium, such as a mixture of air and a gas (or vapor), to be analyzed is introduced into chamber 14 through an inlet 12 using a pump or other air moving device (not shown). The mixture of air and gas is distributed inside the chamber 14 as necessary and drawn out of the chamber 14 through an exhaust outlet 16.

A light beam 18 is emitted from the light source 20, which can be monochromatic or multi-chromatic. The light beam 18 passes through the chamber 14 and the air and gas mixture therein. The light beam 18 is reflected off of one or more holographic reflective pads 22a and 22b on surfaces inside the chamber 14, until ultimately the light beam 18 strikes the detector 24 positioned at an appropriate angle with respect to the holographic reflective pads 22a and 22b. Any contaminants present in the air and gas/vapor mixture will reduce the intensity of the light signal at the detector 24. The light intensity at the detector 24 is used to determine the concentration of the contaminants in the gas. It is appreciated that the inner configuration of the chamber 14 is not limited to a cube shape and that the chamber 14 may be sealed or may be a ported chamber through which a gas or fluid flows. It is also appreciated that contaminant entry and exit into and out of the chamber can be through diffusion membranes. The light path 18 is similarly not restricted to one plane and may span multiple planes as discussed in detail below.

Because different wavelengths will reflect at different angles from the holographic reflective pads 22a and 22b, to function as a prism or not reflect at all depending on the wavelength of the light, proper placement of the detector 24 with respect to the holographic reflective pads 22a and 22b limits the wavelength that reaches the detector 24.

The holographic reflective pads 22a and 22b are holographic images manufactured in the conventional manner known to those skilled in the art and may reflect and/or transmit light. The techniques for generating holographic optical elements and the equipment and materials required are described in detail in reference books, including *Optical Holography*, Collier, Burkhardt & Lynn Academic Press (1971), incorporated herein by reference. The holographic reflective pads 22a and 22b are created to a known reflective angle for a selected wavelength of light. Light at different wavelengths, if reflected at all, would reflect at different angles from the design wavelength. Proper placement of one or more detector 24, and possibly with baffles (see FIG. 2a), would therefore provide a means for wavelength selection, or bandwidth narrowing.

A basic example of an application of the holographic gas analyzer 10 would be a carbon dioxide detector using the methods described herein to generate a reflective surface of sixty (60) degrees and thirty (30) degrees for infra red light with a wavelength of 4.3 microns. It is appreciated that other angles are also possible.

The holographic gas analyzer of the present invention may have a plurality of optional configurations. For example, the number of holographic reflectors encountered by the light path may be increased. By increasing the number of holographic reflectors inside the chamber 14, it is possible to increase the light path folding and therefore increase the ultimate light path length within a fixed chamber volume. The number of holographic reflectors encountered by the light path may be increased in a number of ways.

Figure 2B:
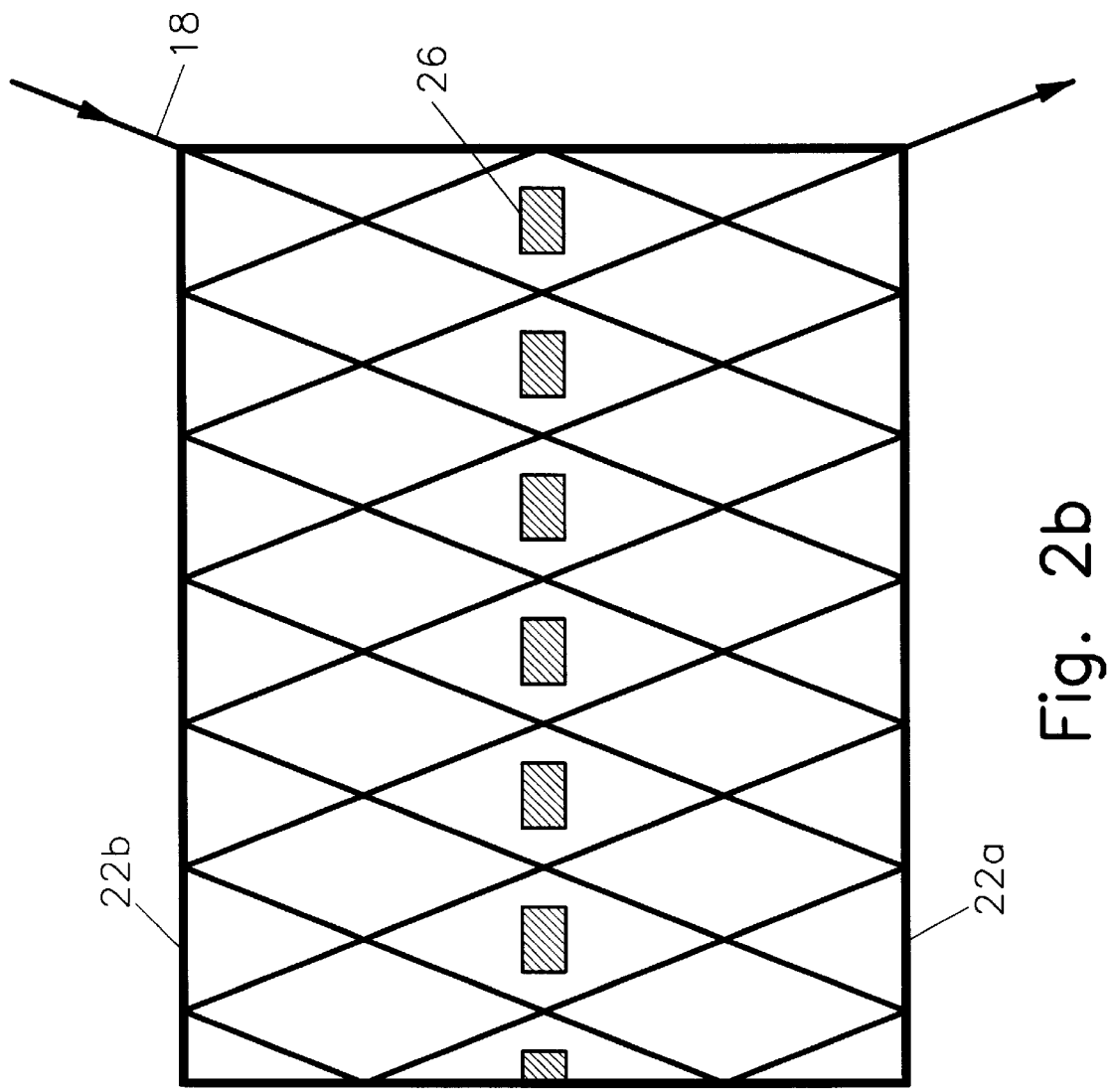

Referring to FIG. 2a and 2b, one method for increasing the number of holographic reflectors is to increase the number of surfaces of the gas/vapor containing chamber having holographic pads. FIG. 2a shows an example of a folded light path on a plane using four reflective inner surfaces of the chamber 14 with at least one holographic reflector pad 22a–22d on each surface of the chamber 14. It is appreciated that it is possible to utilize all or part of the inner surfaces of the chamber 14 to reflect the light path 18.

FIG. 2b is a top view of FIG. 2a showing a complex light path configuration and the placement of optional baffles 26 for providing a means for wavelength selection. There is a sixty (60) degree angle of reflection from the incident light beam to the surface of two holographic reflector pads and a thirty (30) degree angle of reflection from the incident light to the surface of the other two reflector pads. It is appreciated that these angles can vary with the use of different media and wavelengths of light.

Figure 3:
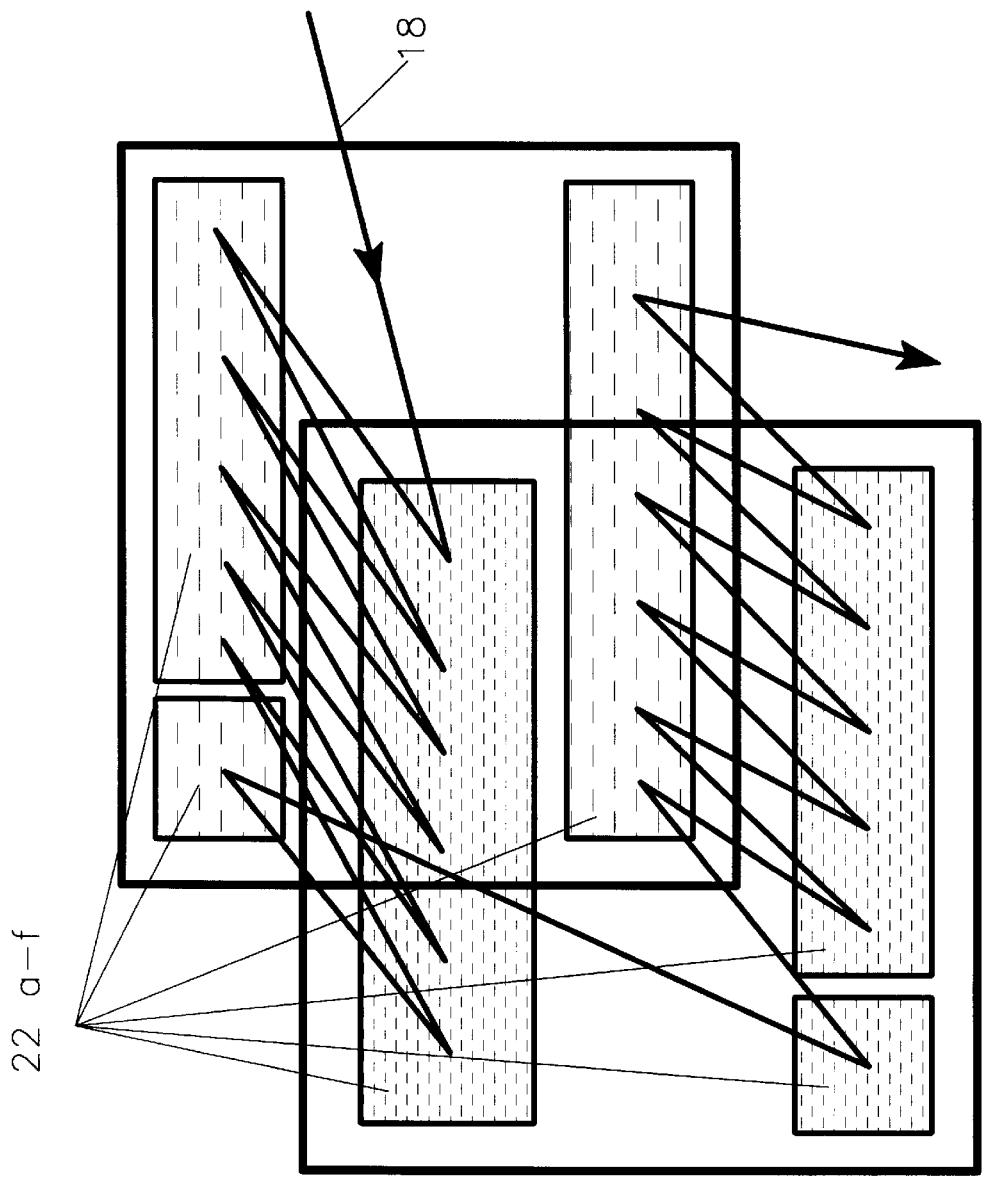
FIG. 3 is a schematic representation of another embodiment of a holographic gas analyzer according to the present invention in which only the reflective surfaces are shown.

Referring to FIG. 3, multiple reflector and/or transmissal holographic reflective pads could be placed on each inner surface of the chamber 14. Each holographic reflective pad could have a different angle of reflection. As shown in FIG. 3, additional holographic reflector pads 22a–f are used to shift a light beam 18 from one plane to another plane. The use of different planes for the reflection of the light path increases the length of the light path within the chamber 14.

Figure 4:
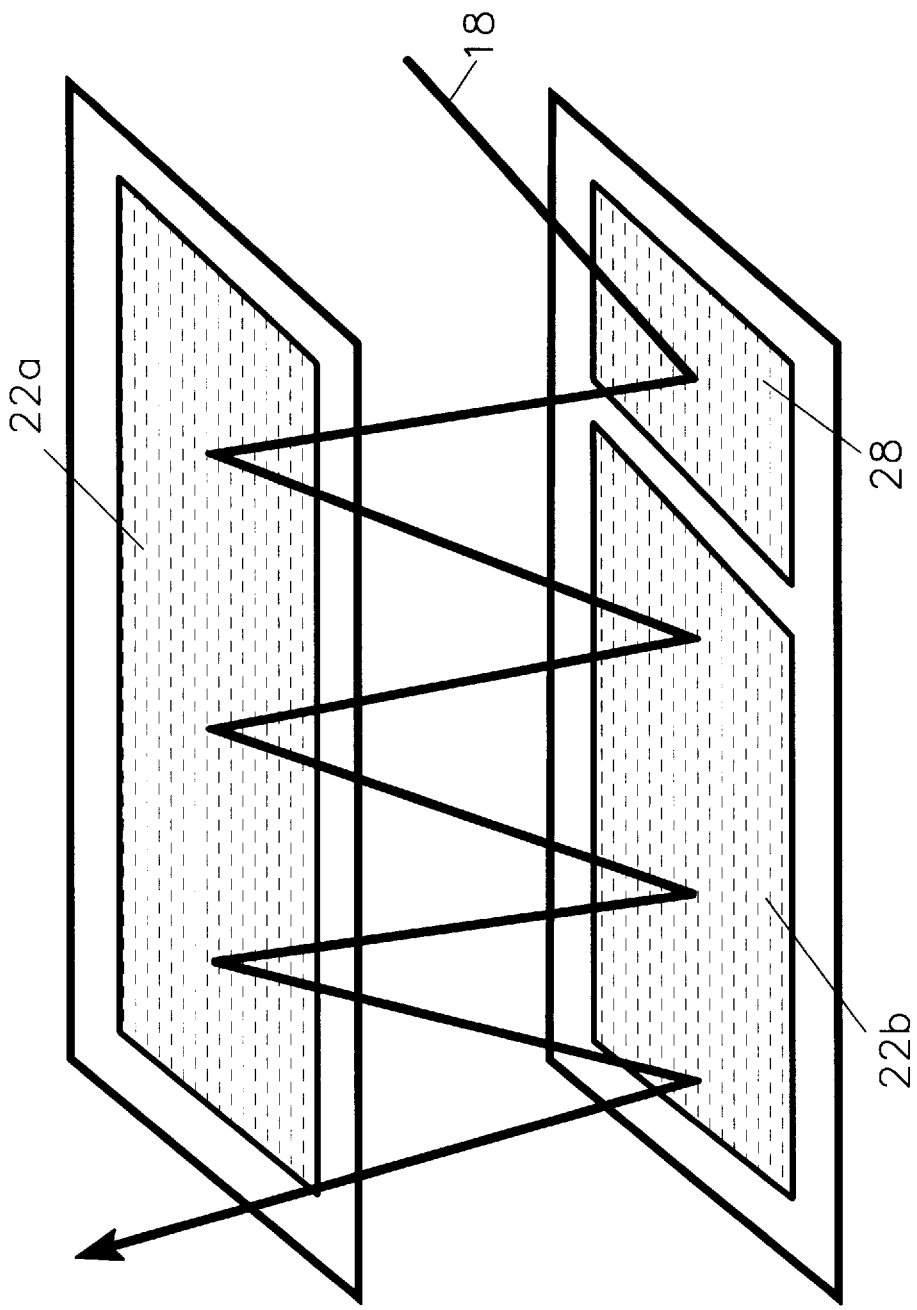
FIG. 4 is a schematic representation of another embodiment of a holographic gas analyzer according to the present invention in which only the reflective surfaces are shown.

Referring to FIG. 4, for circumstances where a more narrow light band width is required, or the wavelength selectivity achieved will be inadequate from reflective selection alone, a holographic diffraction grating pad 28 is incorporated into one of the inner surfaces of the chamber 14. The grating pad 28 could be either a reflective grating or as a transmissive grating. Discrete holographic gratings are known in the art and commercially available.

It is appreciated that other holographic functions could be added to pad functions on multipad surfaces such as light focusing and beam splitting. Multi-chromatic devices can be built for measuring absorbance at multiple peaks for a single compound, or to simultaneously measure exclusive absorbent wavelengths for multiple compounds. These devices can be built using one or more of the following methods.

Figure 5:
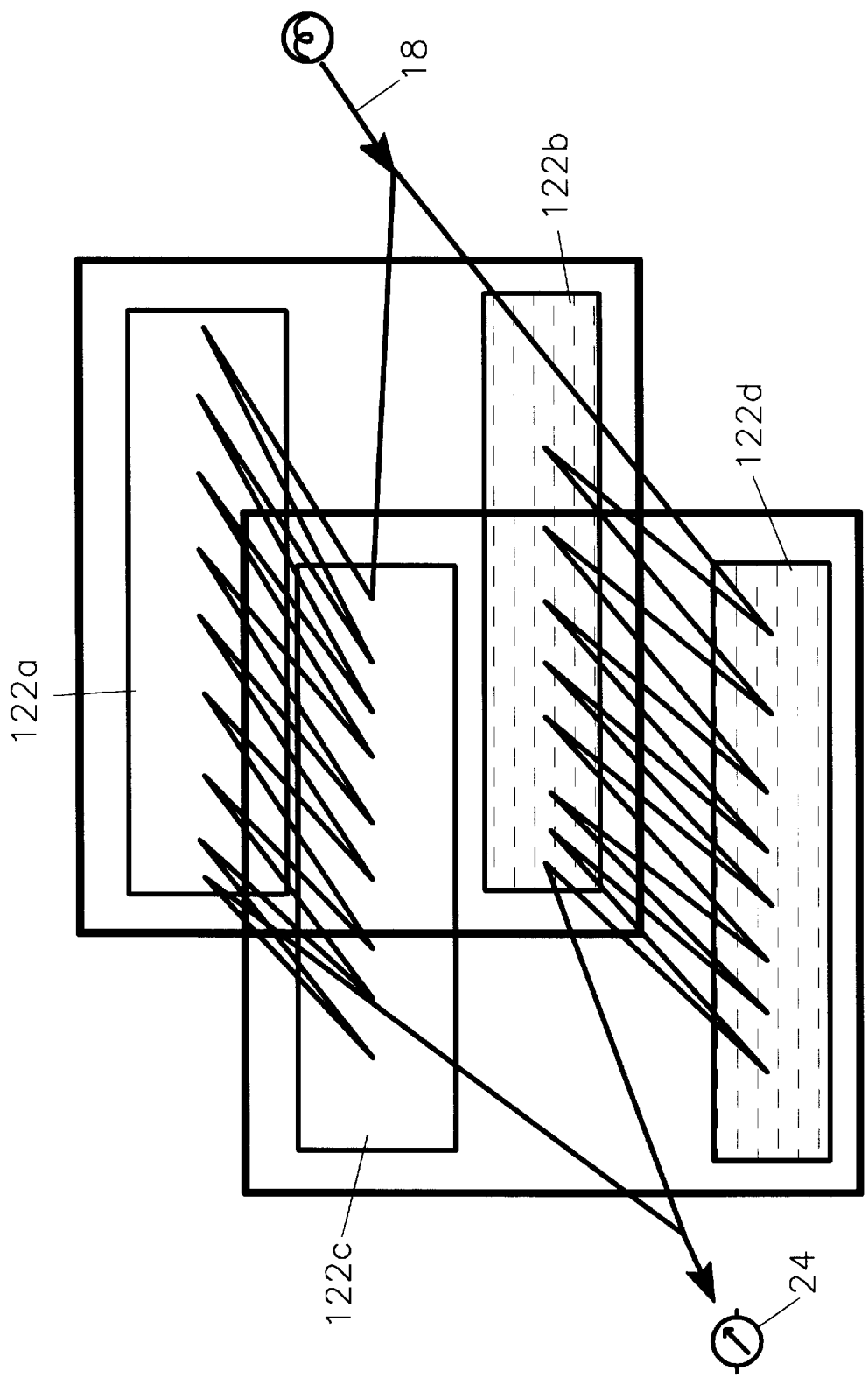
FIG. 5 is a schematic representation of another embodiment of a holographic gas analyzer according to the present invention in which only the reflective surfaces are shown.

Referring to FIG. 5, multiple holographic reflector pads 122a–122d with different design wavelengths could be placed on the inner surfaces of the chamber 14, or on multiple surfaces attached to each other. As necessary, different photographic emulsions can be screened into different areas of the inner surfaces of the chamber 14. Holographic images for different wavelengths can be layered on top of each other. Advantage can be taken of different order reflection surf holograms to produce reflection surfaces which reflect multiple discrete wavelengths at different angles.

Depending on the application, the light beam(s) could be directed to the same or different detectors 24. Alternatively, a multi-chromatic system could use a single detector 24 with beam selection controlled by a stepper motor or vibrating arm.

As holographic optics can be more easily modified for use in harsh environments by application of coatings, or placement of holographic pads behind the surface substrate, such that with proper coatings the present invention could be applied to measurements in static or flowing liquids.

While the present invention has been described in detail with regards to the preferred embodiments, it is appreciated that other variations of the present invention may be devised which do not depart from the inventive concept of the present invention.

What is claimed is:

1. An apparatus for determining the presence of light absorbing matter in a fluid medium, said apparatus comprising:

means for collecting the fluid medium;

a light source;

a light detector; and a plurality of non-dispersive holographic optics positioned relative to said light source and said light detector, at least one of said plurality of holographic optics reflecting at least a portion of light from said light source through said collecting means to another one of said plurality of holographic optics, and one of said plurality of holographic optics reflecting at least a portion of the light to said light detector.

2. The apparatus of claim 1 in which said holographic optics are positioned in an opposite facing relationship.

3. The apparatus of claim 1 in which said holographic optics are on different planes.

4. The apparatus of claim 1 in which said holographic optics conduct light through said collecting means in a path that spans more than one plane.

5. The apparatus of claim 1 further comprising a holographic diffraction grating.

6. The apparatus of claim 1 further comprising a baffle for selecting a wavelength of light from said light source.

7. The apparatus of claim 1 in which said collecting means includes a chamber.

8. The apparatus of claim 1 in which said collecting means includes a flow through collection area for fluid medium.

9. The apparatus of claim 1 further comprising means for protecting said holographic optics.

10. The apparatus of claim 9 in which said protecting means includes a protective coating over said holographic optics.

11. The apparatus of claim 1 light source generates infra red light.

12. The apparatus of claim 11 in which said light detector detects the intensity of infra red light.

13. The apparatus of claim 1 said collecting means comprises a gas inlet and an exhaust outlet.

14. A method for determining the presence of light absorbing matter in a fluid medium, the method comprising the steps of:

collecting the fluid medium;

transmitting light through the fluid medium and to a plurality of non-dispersive holographic optics;

reflecting at least a portion of the transmitted light from one of said plurality of holographic optics to another one of said plurality of holographic optics, and reflecting the transmitted light from one of said holographic optics to a light detector; and detecting the light transmitted from one of said plurality of holographic optics through the fluid medium to the light detector.

15. The method of claim 14 in which the transmitting step includes the substep of transmitting the light in different planes.

16. The method of claim 14 in which the transmitting step includes the substep of transmitting the light through the fluid medium in a path that spans more than one plane.

17. The method of claim 14 in which the transmitting step includes the substep of diffracting the light.

* * * * *